US007268354B2

(12) United States Patent
Heismann et al.

(10) Patent No.: US 7,268,354 B2
(45) Date of Patent: Sep. 11, 2007

(54) METHOD FOR OPERATION OF A COUNTING RADIATION DETECTOR WITH IMPROVED LINEARITY

(75) Inventors: Bjoern Heismann, Erlangen (DE); Silke Janssen, Langensendelbach (DE); Thomas Van Der Haar, Nuernberg (DE)

(73) Assignee: Siemens Aktiengesellschaft, Munich (DE)

( * ) Notice: Subject to any disclaimer, the term of this patent is extended or adjusted under 35 U.S.C. 154(b) by 126 days.

(21) Appl. No.: 11/006,772

(22) Filed: Dec. 8, 2004

(65) Prior Publication Data

US 2005/0123090 A1    Jun. 9, 2005

(30) Foreign Application Priority Data

Dec. 8, 2003    (DE) ................. 103 57 187

(51) Int. Cl.
*G01T 1/00* (2006.01)
*G01D 18/00* (2006.01)
(52) U.S. Cl. .................... 250/395; 250/252.1
(58) Field of Classification Search ............... 250/395, 250/252.1
See application file for complete search history.

(56) References Cited

U.S. PATENT DOCUMENTS

| 5,943,388 | A | 8/1999 | Tümer |
| 6,403,960 | B1 * | 6/2002 | Wellnitz et al. ........ 250/363.09 |
| 6,519,306 | B1 * | 2/2003 | Matsumiya ................ 376/254 |
| 7,139,362 | B2 | 11/2006 | Heismann et al. |
| 2004/0174948 | A1 * | 9/2004 | Kojima et al. ............... 378/19 |

FOREIGN PATENT DOCUMENTS

| DE | 11 65 771 A | 3/1964 |
| DE | 100 20 425 A1 | 12/2000 |
| DE | 102 12 638 A1 | 10/2003 |

OTHER PUBLICATIONS

Petzold W., Messung van Zählverlusten durch Vergleich zweier unabhängiger Zählkreise, Zeitschrift für angewandte Physik; XV. Band, Heft Feb. 1963, p. 158-160.

(Continued)

*Primary Examiner*—David Porta
*Assistant Examiner*—Mindy Vu
(74) *Attorney, Agent, or Firm*—Harness, Dickey & Pierce, PLC

(57) ABSTRACT

A method is for operation of a counting radiation detector, in particular of a counting X-ray detector, with improved linearity, in which each detector element of the counting radiation detector supplies counting pulses at counting rates as a function of a number of radiation quanta which occur per unit time during operation. In the method, the counting rates which are supplied from each detector element or from subsections of the detector element are converted via a functional relationship to actual counting rates or are multiplied by correction factors which are dependent on the magnitude of the counting rates. The correction factors are determined in advance for the respective detector element or for the subsections of it, and any discrepancy (which occurs as a result of a dead time of the detector element, for example) in the counting rates is corrected from the actual number of radiation quanta which arrive per unit time. The method allows the linearity of counting radiation detectors to be improved, particularly at high radiation intensities, so that the linearity condition for X-ray CT systems is also satisfied.

26 Claims, 2 Drawing Sheets

OTHER PUBLICATIONS

Prest M. et al., Frost: a low-noise high-rate photon counting ASIC for X-ray applications. Nuclear Instruments and Methods in Physics Research A 461 (2001) 435-439.

Glenn F. Knoll, Radiation Detection and Measurement, John Wiley & Sons, New York 1979, p. 95-103.

German Office Action dated Feb. 15, 2007.

* cited by examiner

US 7,268,354 B2

METHOD FOR OPERATION OF A COUNTING RADIATION DETECTOR WITH IMPROVED LINEARITY

The present application hereby claims priority under 35 U.S.C. §119 on German patent application number DE 103 57 187.6 filed Dec. 8, 2003, the entire contents of which are hereby incorporated herein by reference.

FIELD OF THE INVENTION

The present invention generally relates to a method for operation of a counting radiation detector, in particular of a counting X-ray detector, with improved linearity. In particular, the method may be one wherein each detector element of the counting radiation detector supplies counting pulses at counting rates as a function of a number of radiation quanta which occur per unit time during operation. The invention also generally relates to a counting radiation detector as well as an X-ray system having a counting radiation detector, which can be operated using the method.

The method is particularly suitable for counting X-ray detectors, such as those which will be used in the future for X-ray computed tomography (CT). However, it can also be used, of course, for other counting radiation detectors in which the problem of inadequate linearity exists owing to the influence of the dead time of the detectors when a large number of radiation quanta arrive per unit time.

BACKGROUND OF THE INVENTION

Examinations are carried out with the aid of computed tomography scanners for many problems in the field of medicine. In this case, a CT scanner includes an X-ray source as well as an X-ray detector which is located opposite the X-ray source and includes a number of detector modules which are formed by individual detector elements. The detector elements are generally arranged in one or more rows alongside one another in order to achieve position-resolved detection of the X-ray radiation. Knowledge about the distribution of the materials within the object being examined can be obtained from the position-resolved measurement of the attenuation of the X-ray radiation caused by the object being examined which is located between the X-ray source and the detector.

In order to detect X-ray radiation, detectors with indirect transducers are known on the one hand, which are composed of a scintillator material, followed by a photodetector. The scintillator converts the incident X-ray radiation to visible radiation, which is then detected by the photodetector. The number of photons produced per X-ray quantum is in this case in general approximately proportional to their quantum energy. As a rule, the electrical signal obtained from the photodetector is integrated over a predetermined time period when using this technique.

Furthermore, specific semiconductor materials are also known for detection of X-ray radiation, in which the incident X-ray radiation produces charge carriers directly. The number of charge carriers produced in these direct transducers per X-ray quantum is in this case in general approximately proportional to their quantum energy.

A counting method is also known for CT scanners, instead of integrating the electrical signal obtained from the transducer. By way of example, DE 102 12 638 A1 discloses a detector module for a CT scanner, which has a number of detector elements which detect the X-ray radiation on the basis of direct transducers. Each detector is connected to a pulse generator in order to produce counting pulses as a function of the received electrical signals. The pulse generator passes the pulses to a counting device, which counts the counting pulses over a time period which can be predetermined, and outputs the result.

When using counting radiation detectors in areas in which the number of radiation quanta to be detected per unit time is very high, the measured counting rate may be corrupted owing to the dead time of the counting detector.

In this context, the expression dead time refers to the time period which the detector requires for processing an event after it occurs. All the other events which arrive during this time period are lost. Particularly at the high rates at which X-ray ray quanta arrive at the detector elements during X-ray CT scanning, the dead time of the detector elements leads to the linearity condition for CT scanning not being satisfied, and thus to the image quality not satisfying the requirements.

SUMMARY OF THE INVENTION

An object of an embodiment of the present invention is to specify a method which allows the operation of a counting X-ray detector, in particular of a counting X-ray detector, with improved linearity.

An object may be achieved by a method. Advantageous refinements of the method will become evident from the following description and from the exemplary embodiments. A counting X-ray detector and an X-ray system with a counting radiation detector, can be operated using the method.

In the method for operation of a counting radiation detector with improved linearity, each detector element in the counting radiation detector supplies counting pulses at counting rates as a function of a number of radiation quanta which occur per unit time during operation. The counting rates which are supplied from each detector element or from subsections of the detector element are converted via a known functional relationship to actual counting rates or are multiplied by correction factors which are dependent on the magnitude of the counting rates, are determined in advance for the respective detector element or for the subsections of it, and correct any discrepancy (which occurs as a result of a dead time of the detector element) in the counting rates from the actual number of radiation quanta (actual counting rates) which arrive per unit time. In this case, the expression a detector element means one pixel of the detector, while subsections of the detector element means possible subpixels into which the detector element can be subdivided, and which each supply their own counting rates.

The radiation detector includes a correction unit which corrects the counting rates using the present method. The X-ray system, in particular an X-ray CT system, in the same way includes a counting X-ray detector and a correction unit, which corrects the counting rates of the X-ray detector using the method of an embodiment.

The method of an embodiment makes use of the fact that the nonlinearity which occurs owing to the dead time in counting detectors is deterministic. The relationship between the measured and the actual counting rate is in this case either already known, or a correction factor can be determined by measurements, and can be tabulated. The correction of the counting rates supplied from the detector using the method of an embodiment results in improved radiation detector linearity, in particular satisfying the linearity requirements for computer tomography applications, so that the image quality when using counting X-ray detectors in this field is improved.

If the counting rate correction is determined with the aid of a comparison measurement, discrepancies from linearity which are caused by other influencing factors may possibly in addition also be corrected by the correction factor.

The counting rate correction in the method of an embodiment can be calculated, for example, from a functional relationship between the actual number of radiation quanta arriving per unit time, that is to say the actual counting rate, and the counting rate supplied from the detector element. In this case, a distinction is drawn between two situations in the behavior of a detector:

(1) "non-paralyzing":

After each detected event, the detector is insensitive for a fixed time $\tau$ ($\tau$=dead time). It cannot record events which arrive during this time.

(2) "paralyzing":

The detector remains sensitive during the dead time as well. The dead time can thus be lengthened by the arrival of a further event.

The theoretical relationship for both situations is known. In the case of non-paralyzing electronics:

$$m = \frac{n}{1+n\cdot\tau} \quad (1)$$

In the case of a detector with paralyzing electronics, the relationship between the measured counting rate and the actual counting rate is as follows:

$$m = n \cdot e^{-n\tau}$$

In this case, m is in each case the measured counting rate, n is the actual counting rate, and $\tau$ is the dead time.

In order to save computation time during the measuring process, correction factors which are dependent on the respective counting rate can be determined and tabulated in advance from the functional relationship.

If this relationship is not known, the correction factors can be determined by a single prior measurement with the aid of a reference detector. In this case, incident radiation is measured at different radiation intensities, in each case with the reference detector and with the counting radiation detector which will be used for the subsequent measurement. The different radiation intensities are in this case preferably chosen such that at least one measurement takes place in a range in which the counting radiation detector is still operating linearly, and numerous further measurements are carried out at intensities at which there is a discrepancy from linearity owing to the dead time, which is also referred to in the following text as the pile-up effect. The reference detector must, of course, in this case operate sufficiently linearly in the respective ranges. The correction values for the various intensities, that is to say the different counting rates of the counting detector, can then be calculated from a comparison of the respectively measured values from the reference detector and from the counting radiation detector.

The correction factors which are obtained at different counting rates are preferably entered in a table in which the counting rates in each case supplied from the counting radiation detector are associated with the associated correction factors. When carrying out the method of an embodiment, the value of the currently supplied counting rate is then in each case looked for in the table, and is multiplied by the associated correction factor. The correspondingly corrected counting rate is provided as an initial value for further processing.

The counting rates supplied from the counting detector may be corrected at different points during the further processing of these counting rates. For example, the relationship between the measured counting rate and the correction factor can be implemented even during the production of the detector in the ASIC of a detector module, so that the counting detector supplies the corrected counting rates directly. If the correction values are not yet known during the production of the detector and have to be determined by measurements later, then the correction steps can be implemented in an evaluation unit, which is connected to the detector during operation.

In the case of a counting X-ray detector which is used in X-ray computed tomography systems, the correction may, for example, be carried out in FPGA electronics (FPGA: Field Programmable Gate Array) in measurement and evaluation electronics (DAS: Data Acquisition System). Furthermore, it is also possible to delay implementation of the correction to the image reconstruction process in the image computer.

BRIEF DESCRIPTION OF THE DRAWINGS

The present method, as well as an X-ray CT system in which the present method is implemented, will be explained in more detail once again in the following text using exemplary embodiments and in conjunction with the drawings, in which.

DETAILED DESCRIPTION OF THE EXEMPLARY EMBODIMENTS

Figure 1:
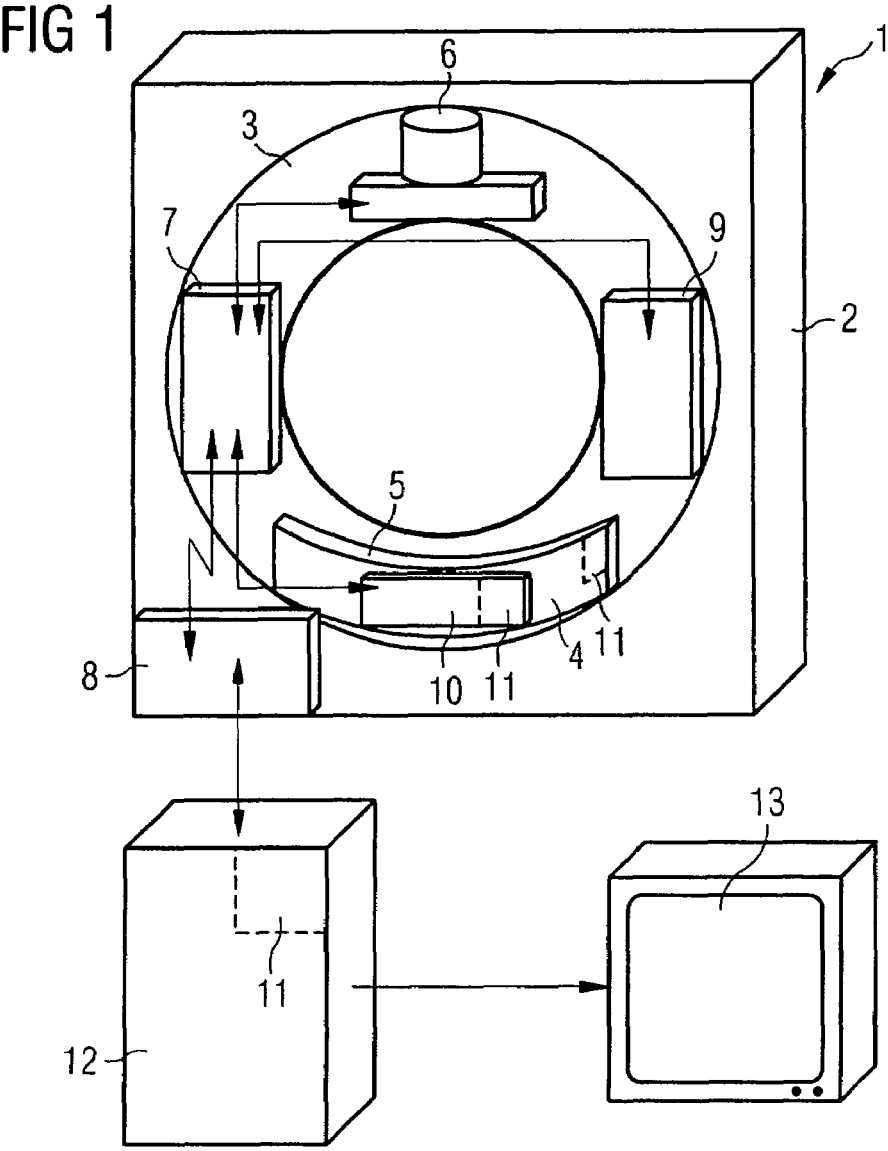
FIG. 1 shows parts of an X-ray CT system with a counting X-ray detector as well as a correction unit in which a method of an embodiment is implemented.

FIG. 1 shows, schematically, an example of parts of an X-ray CT system with a counting X-ray detector (for example based on CZT or CdZnTe) as well as a correction unit 11 in which the present method is implemented. The figure shows the gantry of the CT system 1 with the rotating part 3 as well as the stationary part 2. The X-ray tube unit 6 as well as the detector unit 4 located opposite it can be seen within the rotating part 3. The X-ray tube unit 6 comprises the X-ray tube, a collimator, a focus monitoring device and a device for anode rotation.

The detector unit 4 includes the counting X-ray detector with the individual detector modules 5 and is connected to a measurement and evaluation unit 10, which in the present case comprises an FPGA. Furthermore, a master controller 7 for the rotating part, which may also include dosage modulation, as well as a voltage supply 9 with a radio-frequency generator as well as a voltage source for the X-ray tube unit 6 are arranged on the rotating part 3 of the gantry. The individual control signals and data are transmitted from the master controller 7 to the respective subunits or are received by it, as is indicated by the arrows in FIG. 1.

The master controller 7 on the rotating part 3 is connected to a master controller 8 on the stationary part 2 of the gantry.

The signals and data may be transmitted between the two master controllers via a corresponding pair of sliprings, for example, which are attached to the rotating part 3 and to the stationary part 2 of the gantry. The stationary master controller 8 is in turn connected to the image reconstruction system 12, in which the image is reconstructed for the display on a monitor 13.

During the operation of the X-ray CT system 1, the detector unit 4 supplies counting rates continuously from the individual detector elements 14 in the detector modules 5, and these counting rates are corrected using the method of an embodiment. The correction process in the associated correction unit 11 may, in this case, be carried out either directly in the ASIC of a detector module 5 which includes a number of the detector elements 14 or may be carried out subsequently in the measurement and evaluation unit 10. Furthermore, it is, of course, possible to transmit the uncorrected counting rates to the image reconstruction unit 12 first of all, where the correction unit 11 should be provided. The last-mentioned options are illustrated by the dashed representation of the correction unit 11 in the figure.

Figure 2:
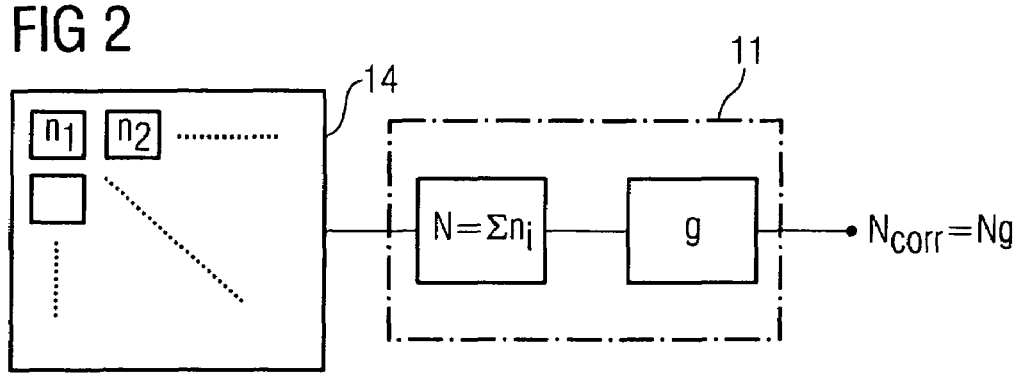
FIG. 2 shows, schematically, the correction process based on an individual detector element in a counting detector.

In the case of detector units 4 in which the correction unit is implemented in the ASIC of the detector modules 5, the correction of the counting rates supplied from the individual detector elements 14 may be carried out differently. For example, the counting rates of the subpixels $n_1 \ldots n_n$ of the detector element 14 (provided that the pixel area is subdivided into subpixels) can first of all be added for each detector element 14, that is to say for each individual pixel of the detector. The counting rates of all the pixels in the detector unit 4, added up from the subpixels, are then multiplied by the correction factor in parallel. This is illustrated by the schematic representation in FIG. 2, in which the individual subpixels $n_1 \ldots n_n$ of a pixel are first of all added up, and the sum is then multiplied by the correction factor g corresponding to this counting rate.

In addition to this refinement, it is also possible to correct the counting rates of the pixels in serial form, that is to say successively. It is also possible to correct the counting rates of the individual subpixels before the addition process.

If the relationship between the measured counting rate and the actual counting rate is not already available when the detector unit is provided, then this relationship must be determined first of all by a prior measurement using the counting detector. In this case, the counting rates supplied during operation are corrected either in the measurement and evaluation electronics 10 or in the image reconstruction unit 12, which contain the appropriate correction unit 11.

Figure 3:
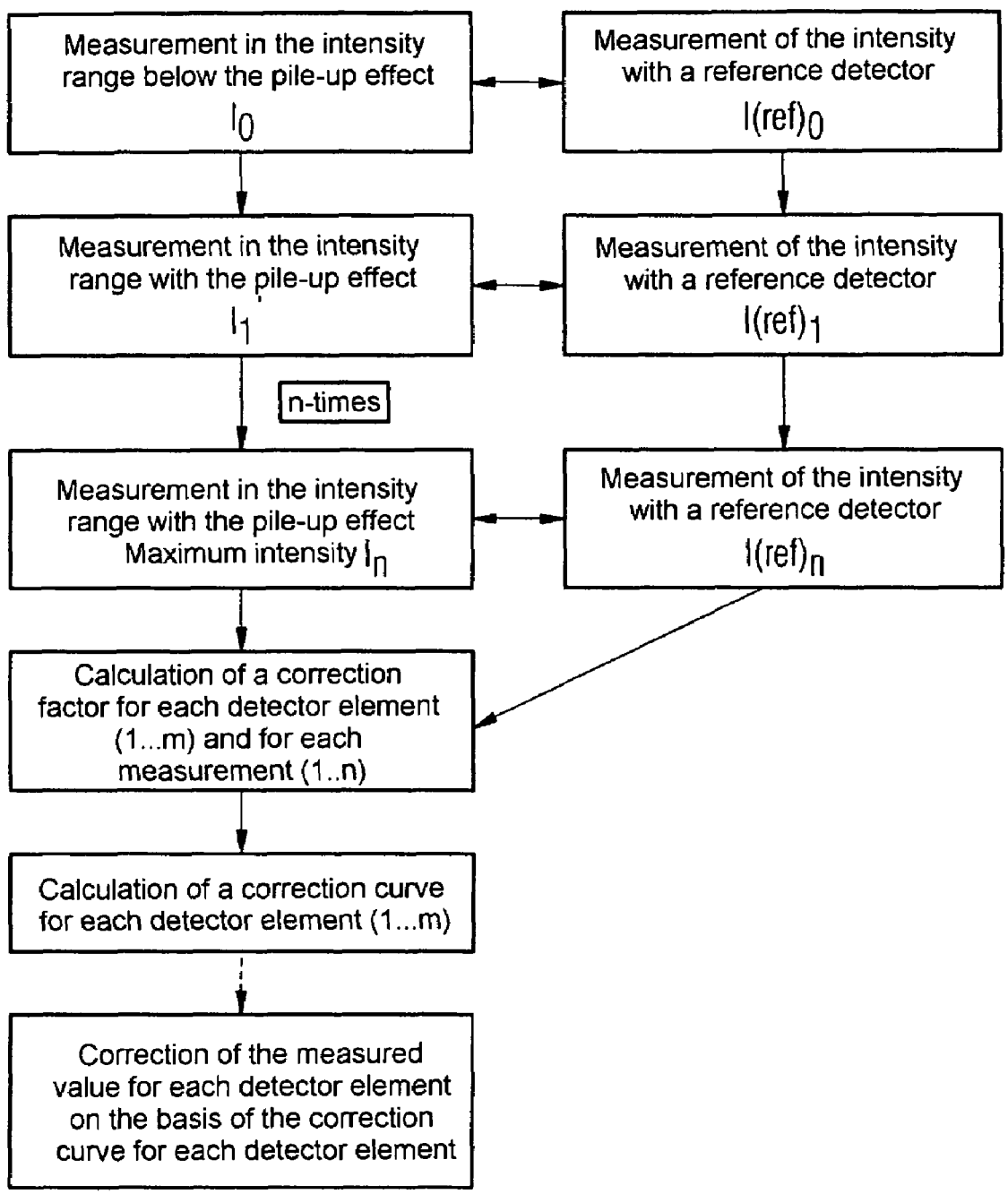
FIG. 3 shows an example of a procedure for creation of the correction table for a method of an embodiment.

The method as shown in FIG. 3 may be used, by way of example, to create the correction table which is required for the correction process. In this method, a reference detector is used in addition to the counting detector, and this reference detector must have no non-linearity, or only a degree of non-linearity which can be corrected well, even at the maximum intensity. This can be achieved, for example, by using a xenon gas detector, a scintillator with a photodiode in the integration mode or a counting detector in the linear range, which can be ensured, by way of example, by shielding in each case.

In this example of the method, a measurement is carried out in the intensity range below the pile-up effect, in each case using the reference detector and using the corresponding counting detector. n measurements are then carried out in the intensity range in which the pile-up effect occurs, as well as one measurement at maximum intensity, in each case with both detectors. Finally, a correction factor for each detector element in the detector and each measurement, that is to say each intensity and counting rate, is determined from a comparison of the respective measured values obtained with the two detectors.

A correction curve or correction table can be created from these values for each detector element in the detector, and can be stored in the correction unit. The greater the number of prior measurements n carried out at different intensities, the more accurately the counting rate can subsequently be corrected when the counting detector is being operated correctly (indicated by the dashed arrow in the figure). At counting rates which are between the counting rates quoted in the table, the associated correction factor may, of course, also be determined by interpolation between the values in the table.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for operation of a counting radiation detector, wherein each detector element or subsections of the detector element of the counting radiation detector is adapted to supply counting pulses at counting rates as a function of a number of radiation quanta which occur per unit time during operation, the method comprising:

determining at least one of a conversion of the counting rates, via a functional relationship, to actual counting rates and a multiplication of the counting rates by correction factors dependent on the magnitude of the counting rates, the determination being made in advance for the respective detector element or subsection;

correcting any discrepancy in the counting rates from the actual number of radiation quanta which arrive per unit time; and outputting the corrected counting rates.

2. The method as claimed in claim 1, wherein the correction factors are derived from a functional relationship between the actual number of radiation quanta which arrive per unit time and the counting rates of the respective detector element or subsection.

3. The method as claimed in claim 2, wherein the correction factors for the detector elements or the subsections of the detector elements of the radiation detector are determined in advance with the aid of a reference detector for different counting rates.

4. The method as claimed in claim 2, wherein the correction is carried out in an ASIC of a detector module which includes the detector elements.

5. The method as claimed in claim 1, wherein the correction factors are taken from a table.

6. The method as claimed in claim 3, wherein the correction factors for the detector elements or the subsections of the detector elements of the radiation detector are determined in advance with the aid of a reference detector for different counting rates.

7. The method as claimed in claim 1, wherein the correction factors for the detector elements or the subsections of the detector elements of the radiation detector are determined in advance with the aid of a reference detector for different counting rates.

8. The method as claimed in claim 7, wherein the correction factors are determined in advance by the following measurements which are carried out both with the radiation detector and with the reference detector:

measurement at an intensity at which no pile-up effect yet occurs in the radiation detector; and measurements at n different intensities at which a pile-up effect occurs in the radiation detector, wherein the reference detector is used such that it has a high degree of linearity for the measurements, and wherein the correction factors for the individual counting rates and detector elements or subsections are calculated by comparing the measured values obtained with the radiation detector and the measured values obtained with the reference detector, in each case at the same intensities.

9. The method as claimed in claim 1, wherein the correction is carried out in an ASIC of a detector module which includes the detector elements.

10. The method as claimed in claim 1, wherein the correction is carried out in FPGA electronics in a measurement and evaluation unit which is connected to the radiation detector.

11. The method as claimed in claim 1, wherein the correction is carried out in an image reconstruction unit of an imaging X-ray system in which the radiation detector is used.

12. The method as claimed in claim 1, wherein the correction is carried out at the same time for all of the detector elements in the radiation detector or a detector module in the radiation detector.

13. The method as claimed in claim 1, wherein the correction for the detector elements in the radiation detector or a detector module in the radiation detector is carried out in a time sequence.

14. A counting radiation detector having a correction unit, which corrects the counting rates using the method as claimed in claim 1.

15. An X-ray system including a counting X-ray detector and a correction unit for correcting the counting rates of the X-ray detector using the method as claimed in claim 1.

16. The X-ray system as claimed in claim 15, wherein the correction unit is implemented in an ASIC of a detector module which includes the detector elements.

17. The X-ray system as claimed in claim 15, wherein the correction unit is implemented in FPGA electronics in a measurement and evaluation unit which is connected to the radiation detector.

18. The X-ray system as claimed in claim 15, wherein the correction unit is implemented in an image reconstruction unit in the X-ray system.

19. The X-ray system of claim 15, wherein the X-ray system is an X-ray CT system.

20. The method as claimed in claim 1, wherein the method is for operation of a counting X-ray detector, with improved linearity.

21. The method as claimed in claim 1, wherein the correcting includes correcting any discrepancy, which occurs as a result of a dead time of the detector element, in the counting rates from the actual number of radiation quanta which arrive per unit time.

22. An X-ray System comprising:

a counting x-ray detector, each detector element or subsections of the counting X-ray detector being useable to supply counting pulses at counting rates as a function of a number of radiation quanta which occur per unit time during operation;

means for determining at least one of a conversion of the counting rates, via a functional relationship, to actual counting rates and a multiplication of the counting rates by correction factors dependent on the magnitude of the counting rates, the determination being made in advance for the respective detector element or subsection; and means for correcting any discrepancy in the counting rates of the counting X-ray detector, from the actual number of radiation quanta which arrive per unit time.

23. The X-ray system of claim 22, wherein the X-ray system is an X-ray CT system.

24. The X-ray system of claim 22, wherein the means for correcting is an ASIC of a detector module which includes the detector elements.

25. The X-ray system of claim 22, wherein the means for correcting is FPGA electronics in a measurement and evaluation unit which is connected to the counting X-ray detector.

26. The X-ray system of claim 22, wherein the means for correcting is an image reconstruction unit in the X-ray system.

* * * * *